United States Patent [19]

Sinofsky

[11] Patent Number: 5,071,417
[45] Date of Patent: Dec. 10, 1991

[54] LASER FUSION OF BIOLOGICAL MATERIALS

[75] Inventor: Edward L. Sinofsky, Peabody, Mass.

[73] Assignee: Rare Earth Medical Lasers, Inc., Dennis, Mass.

[21] Appl. No.: 538,977

[22] Filed: Jun. 15, 1990

[51] Int. Cl.$^5$ .............................................. A61N 5/06
[52] U.S. Cl. ........................................ 606/8; 606/12; 606/16; 606/10; 128/398
[58] Field of Search ................... 606/2, 3, 4, 7, 8, 9, 606/10, 11, 12, 13–17; 128/395–398, 633, 634, 664, 665; 219/121.6–121.62

[56] References Cited

U.S. PATENT DOCUMENTS

| | | | |
|---|---|---|---|
| 4,143,660 | 3/1979 | Malyshev et al. | 128/303.1 |
| 4,316,467 | 2/1982 | Muckerheide | 606/9 |
| 4,641,650 | 2/1987 | Mok | 606/12 |
| 4,644,948 | 2/1987 | Lang et al. | 606/4 |
| 4,672,969 | 6/1987 | Dew | 128/397 |
| 4,719,912 | 1/1988 | Weinberg | 606/4 |
| 4,741,612 | 5/1988 | Birngruber et al. | 351/221 |
| 4,799,479 | 1/1989 | Spears | 128/303.1 |
| 4,854,320 | 8/1989 | Dew et al. | 128/397 |
| 4,917,084 | 4/1990 | Sinofsky | 606/7 |

FOREIGN PATENT DOCUMENTS

| | | |
|---|---|---|
| 214712 | 7/1985 | European Pat. Off. . |
| 618115 | 8/1978 | U.S.S.R. . |
| 618116 | 8/1978 | U.S.S.R. . |
| 1091933 | 10/1981 | U.S.S.R. . |
| 2108282 | 9/1981 | United Kingdom . |

OTHER PUBLICATIONS

Grubbs et al., "J. of Surg. Res.", pp. 112–119 (1988), vol. 45.
Yahr et al., "Surgical Forum," pp. 224–226 (1964).
Schober et al., "Science," pp. 1421–1422 (1986), vol. 232.
Grubbs et al., "J. of Surg. Res.," pp. 112–119 (1988), vol. 45.
Poppas et al., "J. of Urology," pp. 415–417 (1988), vol. 139.
Hemmati, "The NASA/JPL Technical Brief No. NPO-17282/6780", (1988).
Kamiji et al., "Brit. J. of Plastic Surgery," pp. 54–58 (1988).
Popp et al., "Lasers in Surgery and Medicine," pp. 155–158 (1989), vol. 9.
Oz et al., "Lasers in Surgery in Medicine," pp. 248–252 (1989), vol. 9.

Primary Examiner—Stephen C. Pellegrino
Assistant Examiner—Steven J. Shumaker
Attorney, Agent, or Firm—Thomas J. Engellenner

[57] ABSTRACT

Apparatus and methods for laser fusion of biological structures are disclosed employing a laser for delivery of a beam of laser radiation to an anastomotic site, together with a reflectance sensor for measuring light reflected from the site and a controller for monitoring changes in the reflectance of the light of the site and controlling the laser in response to the reflectance changes. In one embodiment, the laser radiation is delivered through a hand-held instrument via an optical fiber. The instrument can also include one or more additional fibers for the delivery of illumination light (which can be broadband or white light or radiation from a laser diode) which is reflected and monitored by the reflectance sensor. Reflectance changes during the course of the fusion operation at one or more wavelengths can be monitored (or compared) to provide an indication of the degree of tissue crosslinking and determine when an optimal state of fusion has occurred.

21 Claims, 5 Drawing Sheets

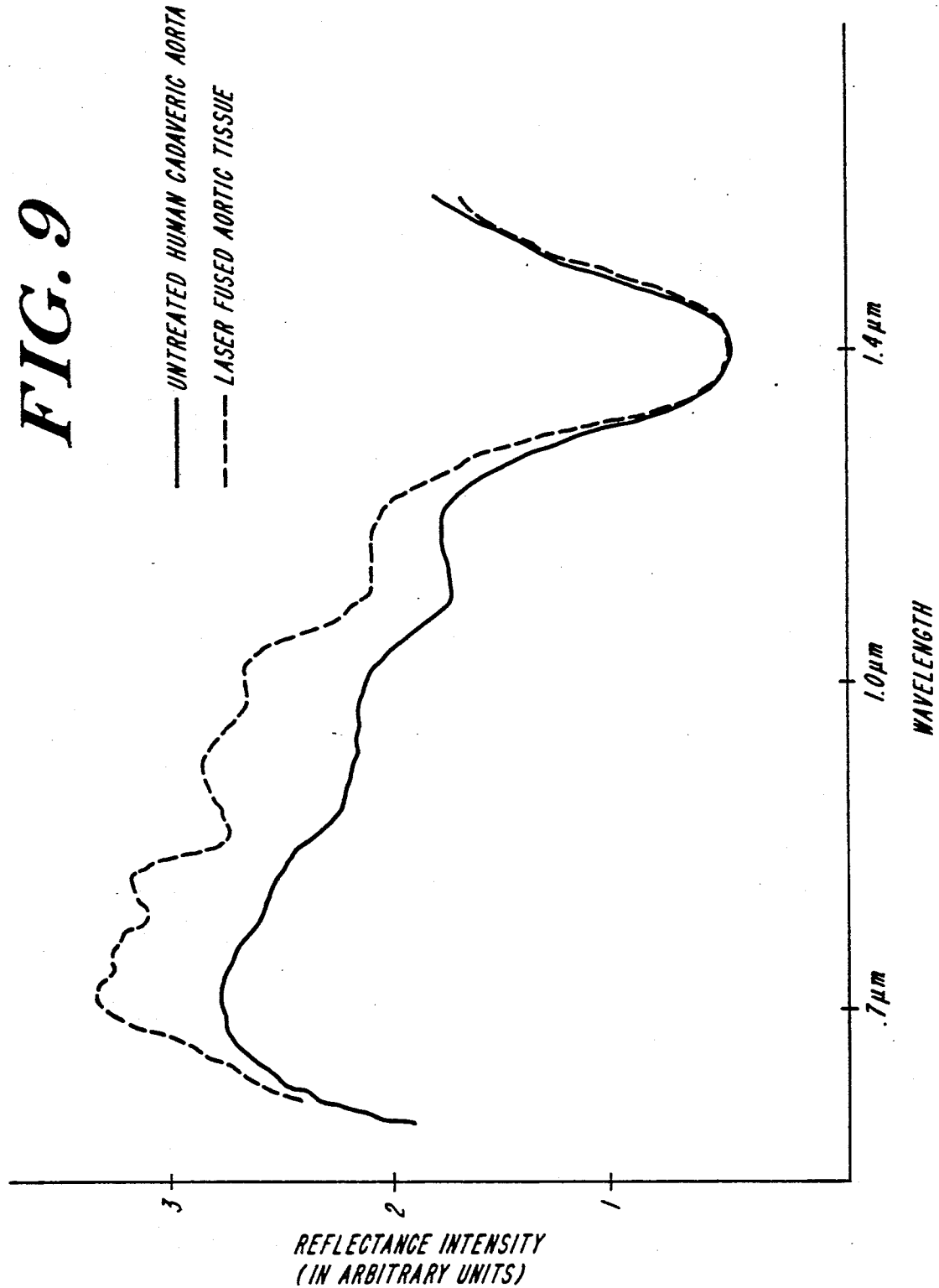

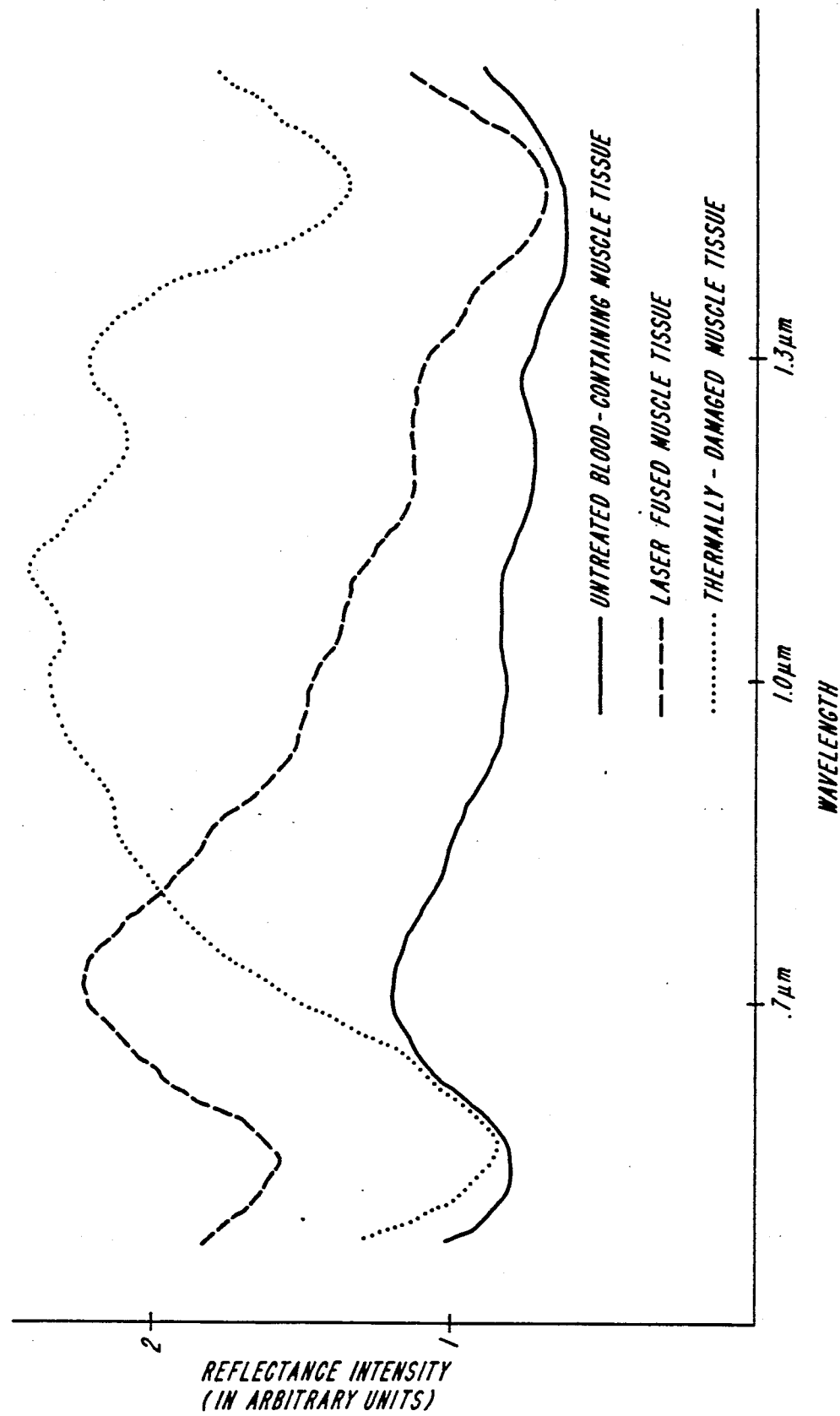

LASER FUSION OF BIOLOGICAL MATERIALS

BACKGROUND OF THE INVENTION

The technical field of this invention is laser surgery and, in particular, laser systems for joining living tissues and promoting the healing of small biological structures.

The conventional approach to joining tissue segments following surgery, injury or the like, has been to employ sutures or staples. While these techniques are often successful, there are a number of limitations inherent in such mechanical approaches. First, the practice of suturing or stapling tissue segments together is limited by the eyesight and the dexterity of the surgeon which can present a severe constraint when anastomosing tiny biological structures. Second, when delicate biological tissues or organs are sutured, even minimal scarring can affect the function of the structure. Finally, suturing can be less than satisfactory, even when properly performed, because of the gaps which are left between the stitches, the inherent weakness of the joint, or the possibility of progressive structural weakening over time.

Various researchers have proposed the use of laser energy to fuse biological tissues together. For example, Yahr et al. in an article in *Surgical Forum*. pp. 224–226 (1964), described an attempt at laser anastomosis of small arterial segments with a neodymium laser. However, the neodymium laser used by Yahr et al. operated at a wavelength of about 1.06 micrometers was not efficiently absorbed by the tissue, requiring large amounts of energy to effect fusion, while also affecting too large of a tissue volume.

Further research on laser fusion involving various alternative laser sources, such as the carbon dioxide laser emitting laser light at about 10.6 micrometers, the argon laser emitting light at about 0.50 micrometers, and the ruby laser emitting light at about 0.70 micrometers, continued to encounter problems. In particular, the output of carbon dioxide lasers was found to be heavily absorbed by water and typically penetrated into water-laden tissue only to a depth to about 20 micrometers. This penetration depth and the resulting bond induced by carbon dioxide laser fusion was too shallow to provide durable bonding in a physiological environment.

Argon and other visible light laser also produced less than satisfactory effects. The output of argon lasers and the like was found to be heavily absorbed by blood and subject to substantial scattering within the tissue. These effects combined to create a narrow therapeutic "window" between a proper amount of energy necessary for laser fusion and that which induces tissue carbonization, particularly in pigmented tissues and tissues that have a high degree of vascularization. Moreover, argon lasers have been particularly cumbersome devices, requiring large amounts of electricity and cooling water.

Recently, the development of new solid state laser sources have made prospects brighter for efficient, compact laser fusion systems suitable for clinical use. Such systems typically employ rare, earth-doped yttrium aluminum garnet (YAG) or yttrium lithium fluoride (YLF) or yttrium-scadium-golilinium-garnet (YSGG) lasers. See, for example, U.S. Pat. Nos. 4,672,969 and 4,854,320 issued to Dew, disclosing the use of a neodymium-doped YAG laser to induce laser fusion of biological materials and to obtain deeper tissue penetration. However, even with such solid state laser sources, the problems of scattering and damage to adjacent tissue remain. The Dew patents disclose the use of computer look-up tables to control the laser dose based on empirical data.

The absorptive properties of biological structures differ considerably from one tissue type to another, as well as from individual to individual, making dosage look-up tables often unreliable. There exists a need for better laser fusion systems that can accurately control the formation of an anastomotic bond to avoid thermal damage and achieve optimal results. A system that could provide real-time feedback to the clinical user would satisfy a long-felt need in the art.

SUMMARY OF THE INVENTION

Apparatus and methods for laser fusion of biological structures are disclosed employing a laser for delivery of a beam of laser radiation to an anastomotic site, together with a reflectance sensor for measuring light reflected from the site and a controller for monitoring changes in the reflectance of the light of the site and controlling the laser in response to the reflectance changes. In one embodiment, the laser radiation is delivered through a hand-held instrument via an optical fiber. The instrument can also include one or more additional fibers for the delivery of illumination light or radiation from a laser diode (which can be broadband or white light or radiation from a laser diode) which is reflected and monitored by the reflectance sensor. Reflectance changes during the course of the fusion operation at one or more wavelengths can be monitored (or compared) to provide an indication of the degree of tissue crosslinking and determine when an optimal state of fusion has occurred.

The present invention permits the creation of anastomoses of biological structures with the optimal use of appropriate laser energy, minimizing the total energy delivered to the site while obtaining maximum bond strength and integrity. The terms "anastomosis" and "anastomotic site" are used herein to broadly encompass the joinder of biological structures, including, for example, incision and wound healing, repair of blood vessels and other tubular structures, sealing of fissures, nerve repairs, reconstructive procedures, and the like.

In the present invention, reflective feedback is used to monitor the state of coagulation of the biological structures so as to allow an optimal dose by either manipulation of the energy level or exposure time, or by controlling the sweep of energy across an exposure path.

Reflectance changes can also be employed by a control means in the present invention to adjust or terminate laser operation. The procedures of the present invention can further employ various "biological glue" materials in either liquid, gel or powder form to enhance the tissue fusion process. Examples of such biological glues include collagen, elastin, fibrin, albumin and various synthetic polymeric materials. Moreover, techniques are disclosed herein for providing increased tensile support along and across the anastomosis by creating coagulated "cross-strips" of annealed biological glue and/or connective tissues that enhance the strength of the bond.

Various laser sources can be employed, including gas, liquid and solid state laser media. Because the present invention permits the user to carefully monitor the laser energy dosage, solid state laser can be utilized instead of the more conventional (and cumbersome) gas lasers. Such solid state laser include optically-pumped (e.g., lamp or diode pumped) laser crystals, diode lasers, and diode pumped optical fibers. Tunable laser sources can also be used to practical advantage in the present invention. Since the feedback control systems disclosed herein eliminate (or reduce) the need for look-up tables, a tunable laser source can be used to full advantage by matching the laser output wavelength with the absorptive and/or dimensional characteristics of the biological structures to be repaired or otherwise joined. In one embodiment of the invention, the laser source can be tuned over at least a portion of a wavelength range from about 1.4 micrometers to about 2.5 micrometers to match particular tissue profiles.

In another aspect of the invention, a real-time display means is disclosed which can be incorporated into a surgical microscope or goggles worn by the clinician during the procedure to provide a visual display of the state of tissue coagulation simultaneously with the viewing of the surgical site. The display can reveal reflectance values at one or more specific wavelengths (preferably, chosen for their sensitivity to the onset and optimal state of tissue crosslinking), as well as display a warning of the onset of tissue carbonization.

In one method, according to the invention, a technique for laser fusion of biological structures is disclosed in which laser energy is applied to join together two or more tissue segments (with or without the use of a biological glue), while the reflectance of light from the irradiated site is monitored. Changes in scattering due to coagulation or crosslinking of the tissue (or biological glue) will cause a reflectance change. In addition, dehydration due to laser exposure also affects the site's reflection. The reflectance can be monitored in real-time to determine the optimal exposure duration or aid as visual feedback in the timing used in sweeping the energy across the anastomosis during the welding procedure.

The method can further be enhanced by coating the entire anastomotic site with a biological glue and then applying laser energy along paths which are generally perpendicular to the joint line. These coagulated strips can have high tensile strength and can provide load support across and along the repair line. These strips are also shallowly crosslinked to the tissue, itself, providing superior bond strength.

The depth of penetration of the laser energy can be controlled in one embodiment by tuning a mid-infrared laser along a range of wavelengths from about 1.4 micrometers to about 2.5 micrometers to adjust the penetration to match the desired weld depth. Tuning can be accomplished, for example, by mechanical or electro-optical variation in the orientation of a birefringent crystal disposed in the laser beam path. This allows the clinician to select a weld depth appropriate to the size and type of structures to be welded. This feature of the invention can be particularly advantageous with delicate biological structures where accuracy is needed to coagulate only what is necessary for temporary strength, while avoiding thermal denaturing of critical structures that cannot function once scarred. In most instances, the patient's body will metabolize the coagulated glue over time simultaneous with (or following) the natural healing of the repair site by physiological processes.

The invention will next be described in connection with certain illustrated embodiments; however, it should be clear by those skilled in the art that various modifications, additions and subtractions can be made without departing from the spirit or scope of the invention.

BRIEF DESCRIPTION OF THE DRAWINGS

FIG. 9 is a graph showing reflectance intensity versus wavelength for a sample of human cadaver aortic tissue before and after laser treatment; and FIG. 10 is another graph showing reflectance intensity versus wavelength for a hemogloblin-containing muscle tissue sample, illustrating the difference between proper fusion and thermal degradation.

DETAILED DESCRIPTION

Figure 1:
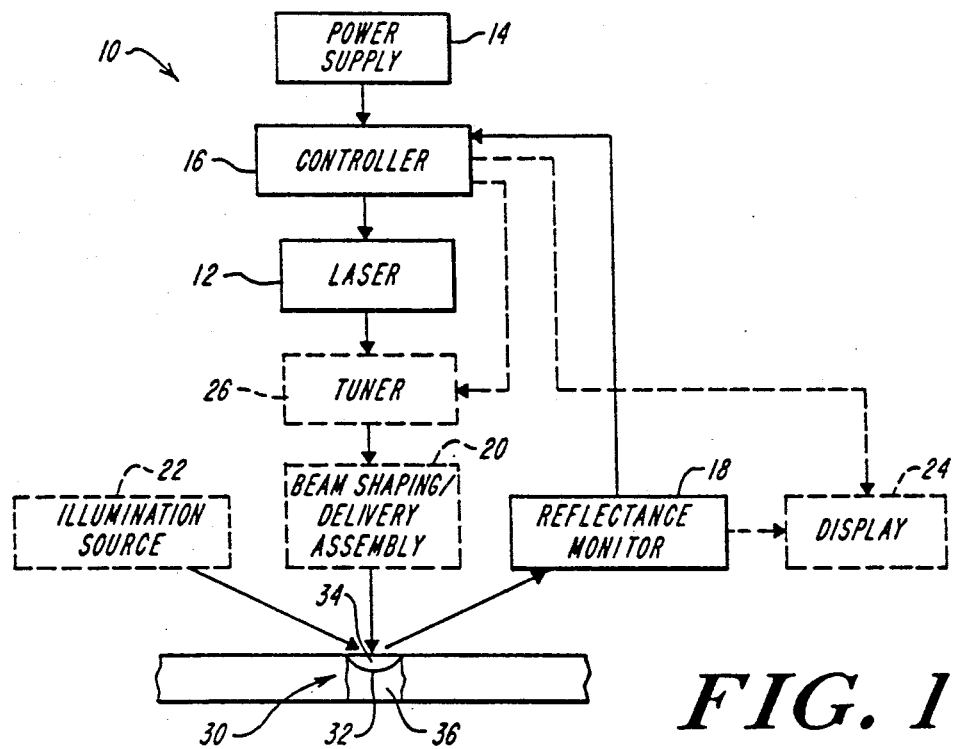
FIG. 1 is a schematic block diagram of a laser tissue fusion system according to the present invention.

In FIG. 1, a schematic block diagram of a laser tissue fusion system 10 is shown, including a laser 12, power supply 14, controller 16 and reflectance monitor 18. The system can further include a beamshaping/delivery assembly 20, illumination source 22, display 24 and tuner 26. In use, the output of laser 12 is delivered, preferably via beamshaping/delivery assembly 20, to an anastomotic site 30 to fuse biological tissue on opposite sides of a fissure or cleavage line 32. As the laser beam irradiates exposure zone 34, preferably with the assistance of a biological glue 36, a crosslinking reaction occurs to fuse the biological tissue in the vicinity of the site 30. The degree of crosslinking is determined by the reflectance monitor 18, which provides electrical signals to controller 16 in order to control the procedure. The reflectance monitor 18 preferably receives light reflected by the site from a broadband or white light illumination source 22. In addition to controlling the laser operation automatically, the reflectance monitor 18 and/or controller 16 can also provide signals to a display 24 to provide visual (and/or audio) feedback to the clinical user. Tuner 26 can also be employed by the user (or automatically controlled by controller 16) to adjust the wavelength of the annealing radiation beam.

Figure 2:
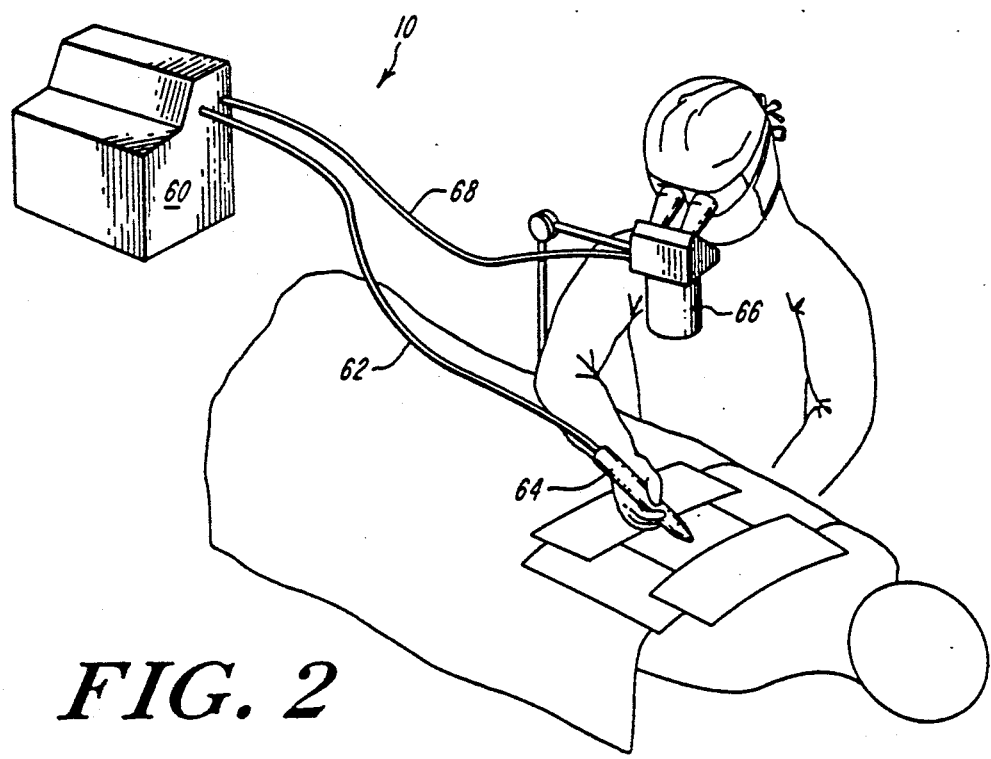
FIG. 2 is a perspective view of a clinical system embodying the principles of the invention.

FIG. 2 provides further schematic illustration of the laser fusion system 10 in use. The electrical and optical components of the system can be housed in a system cabinet 60 suitable for use in an operating room or other clinical environment. The laser output is delivered to the patient by an optical fiber cable 62 (which includes multiple optical fibers as detailed below) and a handpiece 64. The system is preferably used in conjunction with a surgical microscope (or goggles) 66 which are adapted to provide a "heads-up" display to the user. Display signals from the system cabinet 60 are transmitted to the microscope (or goggles) 66 by cable 68.

The present invention can be practiced with a wide variety of laser sources, including both gas and solid state lasers, operating in either continuous wave ("c.w.") or pulsed modes. More specifically, the laser sources can be carbon monoxide, carbon dioxide, argon lasers or various excimer lasers utilizing mixtures of halogen and noble gases, such as argon-flouride, krypton-fluoride, xenon-chloride and xenon-fluoride. Additionally, the laser can be a solid state laser employing a rare, earth-doped Yttrium Aluminum Garnet (YAG) or Yttrium Lithium Fluoride (YLF) or a Yttrium-Scandium-Gadolinium-Garnet (YSGG) laser.

In one preferred embodiment, the laser source is a rare, earth-doped, solid state laser, such as a holmium-doped, erbium-doped or thulium-doped solid state laser of the YAG, YLF or YSGG type which can be operated in a low wattage c.w. or pulsed mode with an output wavelength in the range of about 1.4 to about 2.5 micrometers and a power density of about 0.1 watt/mm$^2$ to about 1.0 watt/mm$^2$. Such laser sources are disclosed in U.S. Pat. No. 4,917,084 issued on Apr. 17, 1990, to the present inventor and incorporated herein by reference.

The absorption of laser energy from such solid state laser sources by biological tissues is relatively high in relation to the absorption of such energy by water, thereby providing an absorption length in the subject's body of about 100 microns or more. Thus, it is possible to operate satisfactorily even with 10-20 micrometers of blood between the handpiece tip and the anastomotic site.

Figure 3:
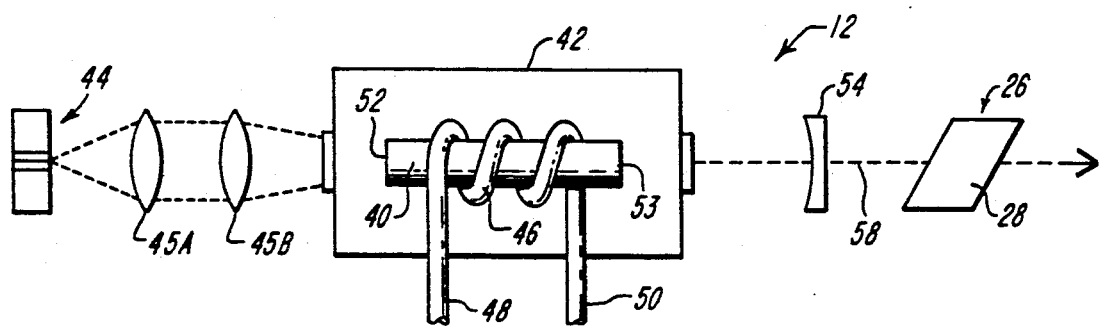
FIG. 3 is a more detailed schematic diagram of a laser source useful in the system of FIG. 1.

FIG. 3 is a schematic illustration of laser source 12, including a solid-state laser crystal 40, vacuum chamber 42 and diode pump source 44. The laser crystal 40 is preferably surrounded by a cooling quartz or fused-silica jacket 46 having inlet pipe 48 and an outlet pipe 50 for circulation of liquid nitrogen or other cryogenic coolant. The laser cavity can be formed by input crystal face coating 52 and partially-reflective output mirror 54.

Generally, the laser crystal 40 is excited by optical pumping, that being, irradiation of the crystal with light from the laser diode 44. (The diode 44 can be cooled by a pumped coolant or employ a heatsink). Both ends of the laser crystal 40 are preferably polished flat. The input face of the crystal 40 is preferably finished with a coating 52 for high transmittance at the pump wavelength and high reflectance of the output wavelength. The other end of the crystal 40 preferably includes an antireflective coating 50 for high transmittal of the output wavelength. The entire cavity of the reflector preferably is evacuated to provide thermal insulation and avoid moisture condensation.

For further details on the construction of cryogenic, solid-state lasers, see, for example, an article by Barnes et al., Vol. 190, *Society of the Photo-Optical Instrumentation Engineers*. pp. 297-304 (1979), NASA/JPL Technical Brief No. NPO-17282/6780 by Hemmati (June, 1988) and above-referenced U.S. Pat. No. 4,917,084, all of which are herein incorporated by reference.

Also shown in FIG. 3 is a tuning element 26 which can include, for example, a birefringent crystal 28 disposed along the beam path 58 at a slight offset from Brewster's angle. The crystal 28 can be tuned electro-optically by application of a voltage, as shown schematically in the figure. Alternatively, the laser wavelength can be tuned mechanically by tilting or rotating the crystal 28 relative to the beam path using techniques well known in the art.

Figure 5:
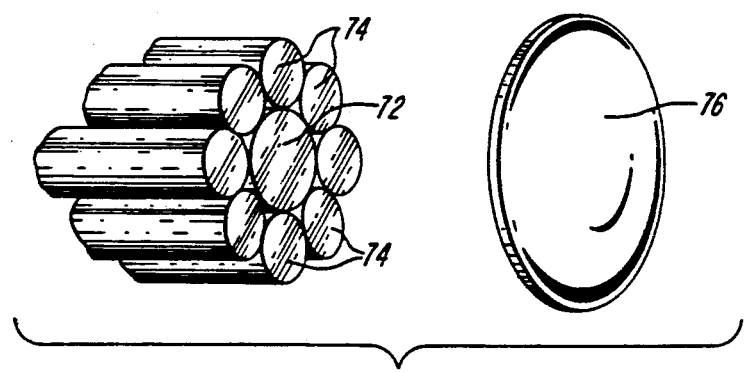
FIG. 5 is a front view of the laser delivery handpiece of FIG. 4.

In FIG., 4 a partial, cross-sectional side view of a handpiece 64 is shown, including a casing 70 adapted for gripping by the clinical user and multiple lumens disposed therein. With further reference to FIG. 5 as well, the handpiece serves to deliver laser irradiation suitable for biological tissue fusion via a central optical fiber 72 connected to laser source, as well as one or more additional illumination fibers 74 for the delivery of illumination light and the transmittal of reflected light. The surgical laser delivery fiber 72 is preferable a low, hydroxyl ion content silica fiber. As shown in FIG. 5, the handpiece 64 can deliver illumination light via fibers 74. In one embodiment, these fibers 74 can also be used to collect reflective light and deliver it to a controller. Alternatively, some of the fibers 74 can be devoted entirely to collection of reflected light. The handpiece 64 can further include one or more lens elements 76, as well as a transparent protective cover element or terminal lens 82.

Figure 4:
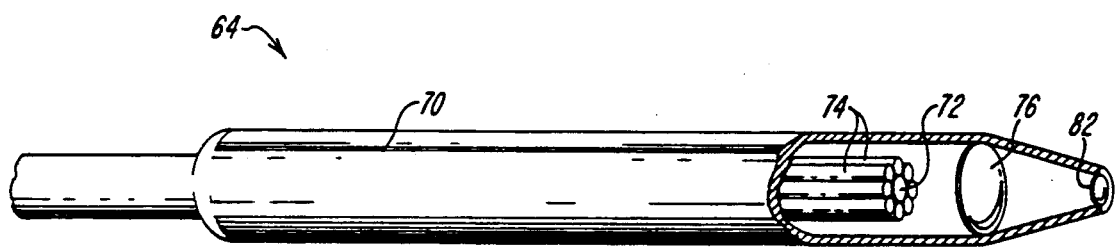
FIG. 4 is a partial, cross-sectional view of a laser beam delivery handpiece according to the invention.
Figure 6:
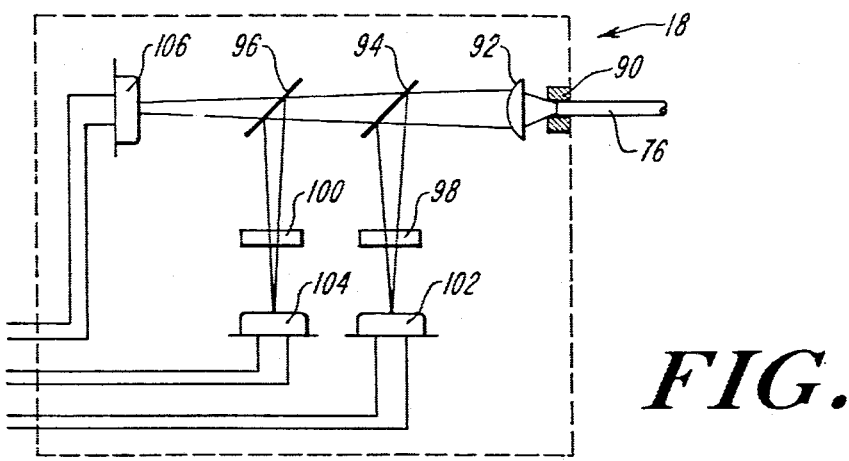
FIG. 6 is a more detailed schematic diagram of reflectance monitor for use in the present invention.

FIG. 6 is a more detailed schematic diagram of a reflectance monitor 18, including a coupling port 90 for coupling with one or more fibers 76 to receive reflectance signals from the handpiece of FIG. 4. The reflectance monitor 18 can further include a focusing lens 92 and first and second beam splitting elements 94 and 96, which serve to divide the reflected light into 3 (or more) different beams for processing. As shown in FIG. 6, a first beam is transmitted to a first optical filter 98 to detector 102 (providing, for example, measurement of reflected light at wavelengths shorter than 0.7 micrometers). A second portion of the reflected light signal is transmitted by beam splitter 96 through a second optical filter 100 to detector 104 (e.g., providing measurement of light at wavelengths shorter than 1.1 micrometers). Finally, a third portion of the reflected light is transmitted to photodetector 106 (e.g., for measurement of reflected light at wavelengths greater than 1.6 micrometers). Each of the detector elements 102, 104, and 106 generate electrical signals in response to the intensity of light at particular wavelengths.

The detector elements 102, 104 and 106 preferably include synchronous demodulation circuitry and are used in conjunction with a modulated illumination source to suppress any artifacts caused by stray light or the ambient environment. (It should be apparent that other optical arrangements can be employed to obtain multiple wavelength analysis, including the use, for example, of dichroic elements, either as beamsplitters or in conjunction with such beamsplitters, to effectively pass particular wavelengths to specific detector elements. It should also be apparent that more than three discreet wavelengths can be measured, depending upon the particular application.) The signals from the detector elements can then be transmitted to a controller and/or a display element (as shown in FIG. 1).

In the controller, signals from the reflectance monitor are analyzed (as detailed below) to determine the degree of crosslinking which is occurring in the biological tissue exposed to the laser radiation. Such analysis can generate control signals which will progressively reduce the laser output energy over time as a particular site experiences cumulative exposure. The control signals can further provide for an automatic shut-off of the laser when the optimal state of crosslinking has been exceeded and/or the onset of carbonization is occurring.

Figure 7:
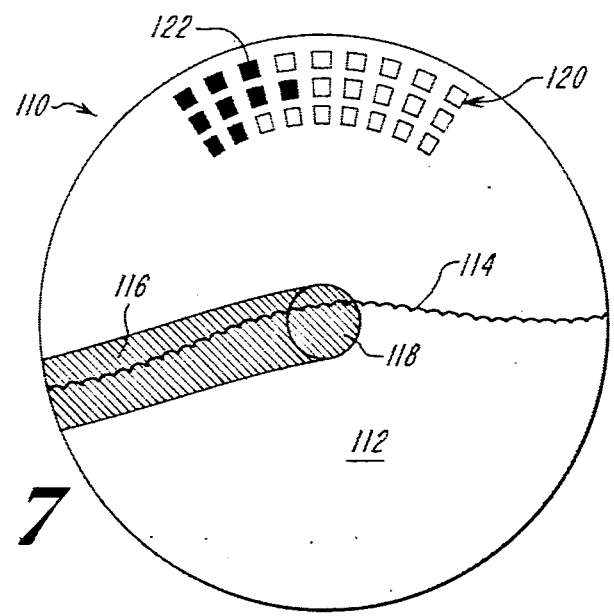
FIG. 7 is a schematic illustration of a clinical eyepiece view showing a "heads-up" display of reflectance measurements according to the invention.

As shown in FIG. 7, the data from the reflectance monitor can also be provided directly to the clinician.

In FIG. 7, a simulated view from an eyepiece 110 is shown in which the field of view 112 includes a fissure or cleavage line 114 dividing separate bodies at an anastomotic site. Also shown within the field of view is a tissue fusion track 116 which has been formed by laser radiation and a present exposure zone 118. Also displayed within the eyepiece 110 is a "heads-up" display of the reflectance values for the reflectance monitor of FIG. 6, including illuminated warning lights 122 which serve to indicate the reflectance intensity at particular wavelengths or other optical data indicative of the degree of crosslinking and/or tissue fusion.

Figure 8:
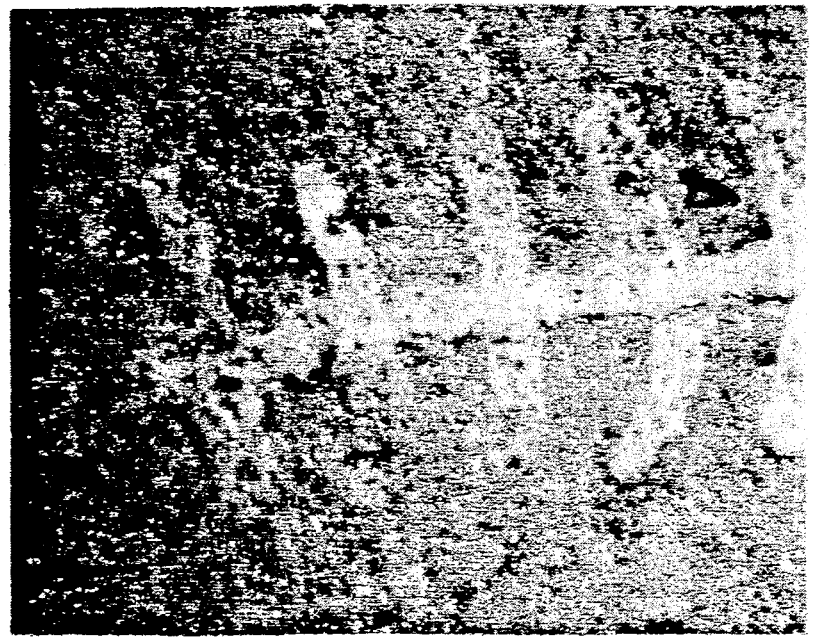
FIG. 8 is a photograph of a laser suture performed on a biological sample.

FIG. 8 is a photograph of a laser suture which was performed using the present invention. The biological material shown in this figure had been surgically cleaved prior to irradiation. As shown, the cleavage line has been fused, and additional "cross-stitches" have been formed by fusion of a biological glue and the target material along liens perpendicular to the cleavage line. The cross stitches impart additional strength to the repair due to their tensile strength and load-bearing properties.

In FIG. 9, the reflectance intensity of light at various wavelengths is shown for a sample of human cadaver aortic tissue before and after laser treatment. As can be seen, there are distinct differences in the reflectance values that allow the present invention to determine when a suitable degree of laser-induced, crosslinking has occurred at the anastomotic site.

In FIG. 10, a further graph of reflectance intensity versus wavelengths for a sample blood-containing muscle tissue is shown which illustrates the differences not only between the untreated tissue and the laser-fund tissue but also reveals the distinct changes on the reflectance profile induced by thermal degradation.

In use, the apparatus of the present invention can be employed to analyze the degree of crosslinking by comparing the reflectance ratios of a site at two or more wavelengths. Preferably, intensity readings for three or more wavelength ranges are employed in order to accurately assess the degree of crosslinking and to ensure that the optimal state is not exceeded. The particular wavelengths to be monitored will, of course, vary with the particular tissue undergoing treatment. Although the tissue type, (e.g., blood-containing tissue or that which is relatively blood-free) will vary, the general principles of the invention, as disclosed herein, can be readily applied by those skilled in the art to diverse procedures in which the fusion of biological materials is desired.

For example, referring again to FIGS. 9 and 10, reflectance spectra are presented before and after the application of laser energy. The X axis indicates wavelengths ranging from about 0.4 micrometers (visible blue-green light) through about 0.6 micrometers (red light), and 1.1 micrometers (near infrared) to about 1.6 micrometers (infrared). As shown in FIG. 10, when carbonization in blood pigmented tissue occurs, the total infrared reflectance (e.g., above 1.0 micrometers) continues to increase while the visible reflectance decreases. Thus, the analyzing circuitry of the controller can be constructed to provide a warning (or automatically shut off the laser radiation) when darkening in the visible wavelengths occurs or when the ratio of visible to infrared values falls below a predefined level.

Moreover, as shown in FIG. 9, when the material to be joined (e.g., aortic tissue) is relatively unpigmented, reliance on changes in the reflectance of visible light can be inaccurate, but infrared reflectance changes (e.g., above 1.1 micrometers) can reliably indicate the degree of crosslinking. (Lack of change in the visible reflectance is one of the reasons that tissues of this type are difficult to crosslink, as no change in the target's visible properties are observed until the tissue is overexposed to laser energy.) Consequently, the analyzing circuitry can monitor infrared reflectance changes (e.g., greater than about 1.0 micrometers) as an indicator of proper crosslinking.

Finally, the reflectance sensor can also be used as a proximity monitor to ensue that the laser is in fact disposed at a proper distance from the anastomic site. By measuring total reflectance (over the entire visible-infrared range or a portion thereof), a sudden drop in the reflectance value will typically be related to incorrect placement of the handpiece. Thus, the analyzing circuitry can sense the changes in reflectance and generate a warning to the user (or automatically shut off the system) until proper placement is achieved.

What is claimed:

1. An apparatus for joining biological materials comprising:
    a laser means, including a laser source and optics, for delivering a beam of laser radiation to an anastomotic site;
    reflectance sensor means for measuring the intensity of infrared light reflected from said site while illuminating the site by a light source;
    monitoring means connected to the reflectance sensor means for monitoring changes int he intensity of infrared light reflected from said site;
    analyzing means connected to said monitoring means for determining the degree of crosslinking of said biological materials based upon said monitored changes and for generating a signal representative of the degree of crosslinking;
    control means connected to said analyzing means and laser means for controlling the output of the laser means in response to said crosslinking signal.

2. Apparatus according to claim 1 wherein the apparatus further includes an illumination means, including optics integrated in a common housing with the optics of said laser means, for illumination of the anastomotic site.

3. Apparatus according to claim 2 wherein the illumination means is a white light source.

4. Apparatus according to claim 1 wherein laser source generates an output wavelength ranging from about 1.4 to about 2.5 micrometers.

5. Apparatus according to claim 4 wherein the laser source further comprises a holmium-doped laser.

6. Apparatus according to claim 4 wherein the laser source further comprises an erbium-doped laser.

7. Apparatus according to claim 4 wherein the laser source further comprises a thulium-doped laser.

8. Apparatus according to claim 1 wherein the apparatus further comprises a tuning means optically aligned with the laser means and disposed within the path of the laser radiation for tuning the output beam of said laser means.

9. Apparatus according to claim 1 wherein the optics of the laser means further comprises a laser beam delivery means for delivering a beam of laser radiation from the laser means to a handpiece.

10. Apparatus according to claim 9 wherein the beam delivery means further comprises an optical fiber of silica with reduced hydroxyl ion content.

11. Apparatus according to claim 1 wherein the reflectance sensor means further comprises a filter means for filtering the reflected light in order to obtain intensity measurements at a plurality of wavelengths.

12. Apparatus according to claim 11 wherein the analyzing means determines the degree of crosslinking based upon changes in at least one of said intensity measurements.

13. A method for joining bilogical materials comprising:
    delivering a beam of laser radiation to an anastomotic site;
    measuring the intensity of infrared light reflected from said site; and
    controlling the beam of laser radiation during irradiation of said site in response to monitored changes int he intensity of the infrared light reflected from the site to achieve crosslinking of ht biological materials without thermal damage.

14. The method of claim 13 wherein the method further comprises illuminating the anastomotic site with a broadband illumination source.

15. The method according to claim 13 wherein the method further comprises tuning the output wavelength of the beam of laser radiation to vary depth of penetration and achieve a desired absorption profile in a particular biological material.

16. The method according to claim 13 wherein the method further comprises analysing the degree of crosslinking within an exposure zone based on measurements of reflectance intensity at a plurality of wavelengths.

17. The method of claim 13 wherein the method further comprises applying a biological glue to the anastomotic site prior to laser irradiation.

18. The method of claim 17 wherein the method further comprises employing said laser irradiation to fuse the biological materials and glue together along a repair line.

19. The method of claim 13 wherein the method further comprises employing the laser radiation to provide cross stitches generally perpendicular to a repair line.

20. The method of claim 13 wherein the method further comprises measuring the intensity of visible light and analyzing changes in the intensity of said visible light to determine the onset of carbonization in the biological material at the site and controlling the laser radiation in response to the analysis.

21. A method for joining biological materials comprising:
    delivering a beam of laser radiation to an anastomotic site;
    applying said laser radiation along a repair line to join adjacent regions of biological material by laser-induced crosslinking; and
    further applying the laser radiation along lines generally perpendicular to said repair line to form cross stitches which increase the bonding strength along said repair line.

* * * * *